US006346103B1

(12) United States Patent

Korsec et al.

(10) Patent No.: US 6,346,103 B1

(45) Date of Patent: Feb. 12, 2002

(54) HEATING ACUPUNCTURE NEEDLE

(75) Inventors: Philippe Korsec, 13 rue de la Glaciere 67300, Schiltigheim; Jean-Paul Hoessler, Durningen, both of (FR)

(73) Assignee: Philippe Korsec, Schiltigheim (FR)

(*) Notice: Subject to any disclaimer, the term of this patent is extended or adjusted under 35 U.S.C. 154(b) by 0 days.

(21) Appl. No.: 09/284,837

(22) PCT Filed: Oct. 22, 1997

(86) PCT No.: PCT/FR97/01893

§ 371 Date: Apr. 21, 1999

§ 102(e) Date: Apr. 21, 1999

(87) PCT Pub. No.: WO98/17225

PCT Pub. Date: Apr. 30, 1998

(30) Foreign Application Priority Data

Oct. 22, 1996 (FR) ........................................ 96 13011

(51) Int. Cl.[7] ........................................ A61B 17/36

(52) U.S. Cl. ........................ 606/29; 606/189; 128/907

(58) Field of Search ............................ 606/189, 188, 606/13, 185, 29–34, 44; 600/548; 607/115; 128/907; 219/226–279

(56) References Cited

U.S. PATENT DOCUMENTS

| | | | | | |
|---|---|---|---|---|---|
| 3,625,202 | A | * | 12/1971 | Oyoshirhara | 128/329 |
| 3,938,526 | A | * | 2/1976 | Anderson et al. | |
| 5,094,242 | A | | 3/1992 | Gleason et al. | |
| 5,211,175 | A | * | 5/1993 | Gleason et al. | 128/642 |
| 5,223,124 | A | * | 10/1999 | Ege | 204/418 |
| 5,969,238 | A | * | 10/1999 | Fischer | 73/105 |

FOREIGN PATENT DOCUMENTS

| | | |
|---|---|---|
| WO | WO 95/20935 | 8/1995 |

* cited by examiner

*Primary Examiner*—Michael H. Thaler

(74) *Attorney, Agent, or Firm*—Young & Thompson

(57) ABSTRACT

A heating acupuncture needle, comprising a source of external energy which heats a heating structure, the heating structure extending over at least most of the length of the needle and comprising an electrically conductive envelope surrounding the needle but leaving an upper end of the needle uncovered. The needle has a tip which is uncovered by the electrically conductive envelope, or which in another embodiment is uncovered. There is an electrically insulating layer between the electrically conductive envelope and the needle, which may surround the tip of the needle or may expose the tip of the needle.

9 Claims, 2 Drawing Sheets

HEATING ACUPUNCTURE NEEDLE

FIELD OF THE INVENTION

The present invention relates to the field of medicine, more particularly to traditional Chinese medicine, namely acupuncture and moxatherapy and has for its object a heating acupuncture needle.

BACKGROUND OF THE INVENTION

Acupuncture with the use of heating means at the acupuncture point is a traditional technique which generally uses wormwood or another means, most often vegetable, brought to very high temperature, namely consuming itself by charring.

At present, this treatment technique is used, as explained more particularly in U.S. Pat. No. 3,875,944, by means of an acupuncture needle provided at its upper portion with a sleeve for reception of incandescent moxa or wood charcoal. Because of the very great heat given off by the moxa or the wood charcoal, there is produced a transmission of heat by conduction of the sleeve toward the end of the needle, this supplemental heat being adapted to carry out a heating in depth of the human tissues or all the length of penetration of the needle with however progressive decrease of thermal energy, corresponding to progressive decrease of the temperature of the sleeve toward the point of the needle.

This traditional treatment technique however has the drawback, on the one hand, of high risk of burning the skin, on the other hand of giving rise to a large and troublesome emission of smoke and, finally, of not permitting the use of moxa in a permanent and/or ambulatory manner.

Thus, the arrangement of the wormwood or incandescent wood charcoal on the sleeve provided at the end of the acupuncture needles has high risk of contacting said wormwood or wood charcoal directly with the skin and hence of deeply burning the latter, due to the temperature of incandescence of the wormwood or of the wood charcoal which is of the order of 700° C. It is therefore necessary, on the one hand, that the practitioner arrange the acupuncture needles such that the heat source remains at least two centimeters from the skin and, on the other hand, that during treatment, the patient remains absolutely motionless so as to avoid any risk of contact between the wormwood or the wood charcoal and the skin following a movement of the needle into its flexible nature. This also gives rise to the need to carry out a depth of acupuncture of at least 5 mm, which prevents the treatment of regions difficult to puncture, such as the scalp and the face. Similarly, the treatment of hairy regions can require preliminary shaving of the skin.

Moreover, certain types of skin have a particular sensitivity to the heat produced by the wormwood that is consumed.

The release of smoke is also a great drawback, not only because of the difficulty thus occasioned, but also because said smoke, which contains toxic elements, can be the cause of headaches and other symptoms, which requires the use of evacuation systems such as hoods.

Finally, in view of the mentioned risks, it is impossible to envisage the use of moxa continuously and/or in an ambulatory manner with traditional means, which requires the continuous presence of the practitioner during all the treatment, which can have a duration of 30 minutes or more.

It has also been proposed, in EP-A-552 482, to carry out heating at the point of acupuncture by means of a heating source of the electric type, said heating source co-acting with an application surface of the heat that can be disposed at the acupuncture point. Such a device of course permits heating without risk and perfectly controlled at the point of acupuncture but however the device according to this EP-A-552 482 does not permit heating at a regular depth, over all the depth, of the human tissue.

As a result, a regulation of the human thermal phenomena, such as is obtained by traditional means, is only difficultly achieved.

To avoid these drawbacks, there has been proposed, in FR-A-2 715 838 and in PCT/FR95/00145, a heating acupuncture needle provided with an external heat source co-acting with heating means, which is integrated with the needle over all the length of the latter and is present in the form of a thermal conductor or a resistive wire, of which one end is flush with the upper end of the head of the needle and is in contact with a conductive wall of the heat source.

Such a needle permits carrying out a heating, subdermally, at the acupuncture or reflexotherapy point, such that it is possible to carry out a non-exclusive single point stimulation, of variable depth and extent by means of a portable and self-contained assembly requiring no external connection by means of wires or other connectors.

However, because of the provision as heat production and/or transmission means, of a thermal conductor or of a resistive wire in the body of the needle, this latter is less flexible, which leads to less efficiency.

OBJECT OF THE INVENTION

The present invention has for its object to overcome the drawbacks of the known heating acupuncture needles, by providing such a needle having flexibility comparable to that of conventional acupuncture needles, whilst permitting results of regular and constant penetration of the heat into the human tissue at least comparable to those obtained by traditional acupuncture means with moxa.

SUMMARY OF THE INVENTION

To this end, the invention has for its object a heating acupuncture needle provided with an external energy source co-acting with a heating means forming an integral part of the needle and extending over all the length of the latter, characterized in that the heating means is present in the form of a thin resistive envelope surrounding the body of the needle over all its surface except the upper end of its head, which remains uncovered.

BRIEF DESCRIPTION OF THE DRAWINGS

The invention will be better understood from the following description, which relates to a preferred embodiment, given by way of non-limiting example, and explained with reference to the accompanying schematic drawings, in which.

DETAILED DESCRIPTION OF THE INVENTION

Figure 1:
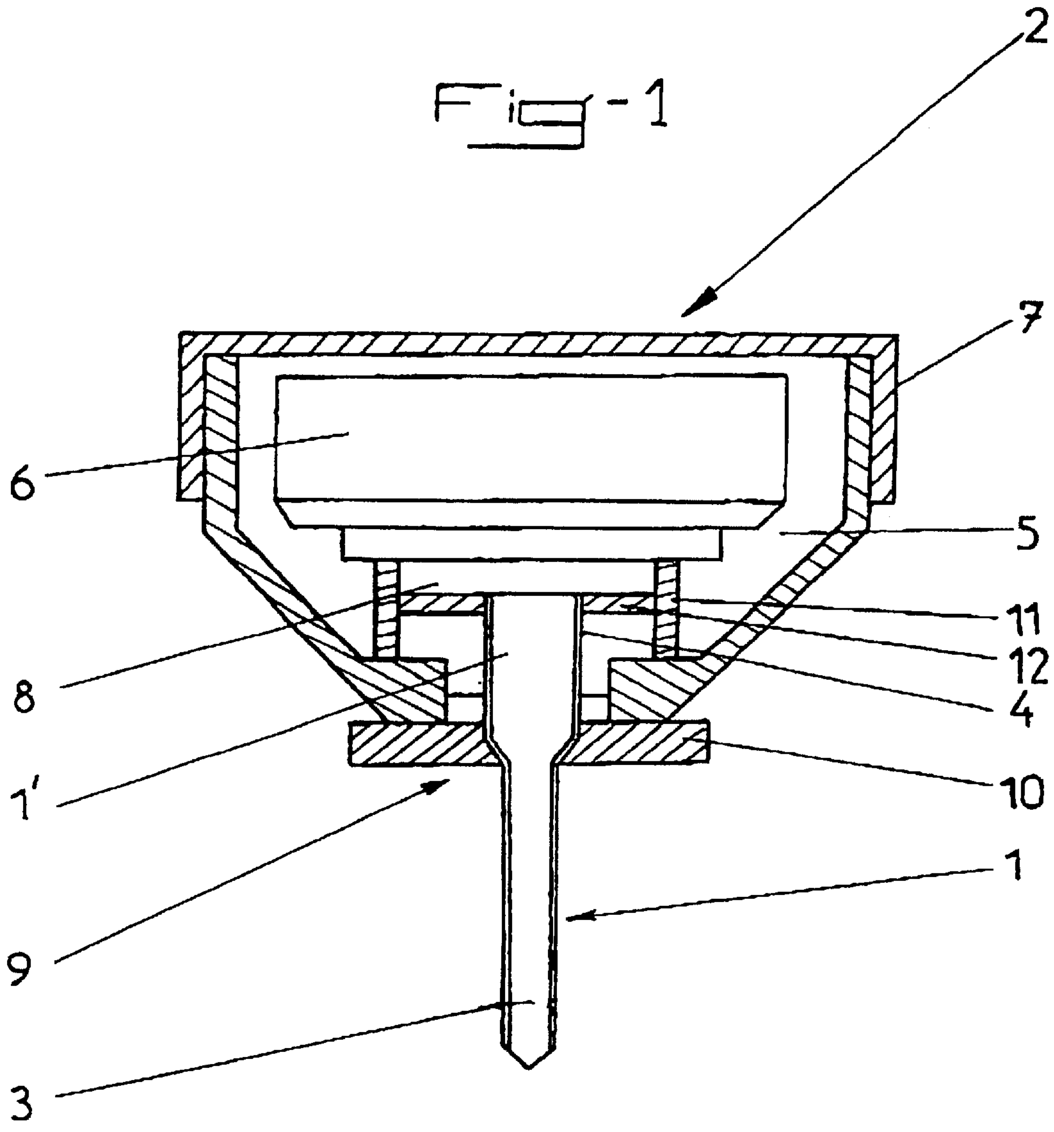
FIG. 1 is an elevational and cross-sectional view, greatly enlarged, of a needle according to the invention.

FIG. 1 of the accompanying drawings shows a heating acupuncture needle 1 provided with an external energy source 2 which co-acts with a heating means 3 forming an integral part of needle 1 and extending over all the length of this latter.

According to the invention, the heating means 3 is present in the form of a thin resistive envelope surrounding the body of the needle 1 over all of its surface except the upper end of its head 1', which remains uncovered.

Figure 2:
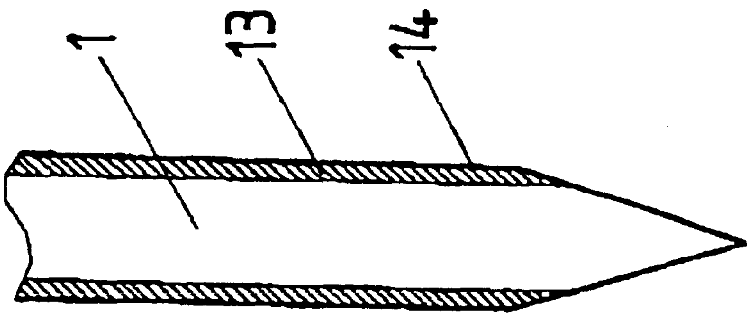

According to one characteristic of the invention, this resistive envelope is preferably constituted by a thin insulating layer 13 entirely surrounding the body of the needle 1 except the upper end of the head 1' and of the end of the point and itself covered, over all of its surface, with a very thin layer 14 that is conductive of the electricity, this conductive layer 14 also covering the end of the point which is not provided with the thin insulating layer 13. This characteristic appears in the cross-sectional detailed view greatly enlarged of one end of a needle according to FIG. 2 of the accompanying drawings, in which the means 3 is shown by two lines extending on opposite sides of the body of needle 1, whilst the very thin electrically conductive layer 14 also surrounding the point is shown by a single line parallel to this point. To this end, the thin insulating layer 13 can preferably be constituted by an epoxy, polyurethane or fluorinated resin, of the tetrafluoroethylene type, and the electrically conductive layer 14 can be a film of metal, particularly biocompatible metal.

So as to obtain good flexibility of the needle, the thickness of the composite layer forming the heating means 3 is preferably low relative to the diameter of the body of the needle and is preferably less than 0.1 of the diameter. Thus, the needle according to the invention will have a flexibility substantially comparable to that of a conventional acupuncture needle.

The resins used are preferably flexible and adhere well to the steel constituting the body of the needle 1. Preferably, these resins are biocompatible. Moreover, these resins have a viscosity permitting their deposition in the form of very thin layers and they are metallizable.

The covering of the body of needle 1 with a layer of resin is carried out by quenching or any other technique of coating and the ultimate deposition of the conductive layer 14 is carried out by chemical means or by physical means.

By way of example, the insulating layer 13 is preferably a polyurethane resin of the type of that known by the commercial name ESTHANE 5715P of the BF GOODRICH company. This resin permits obtaining adherent, smooth and insulating deposits.

Figure 3:
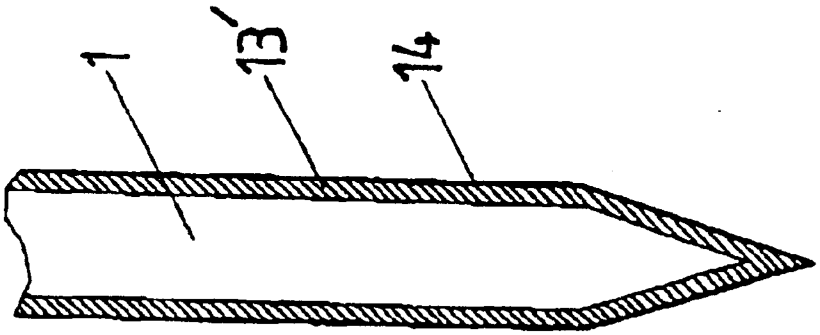
FIGS. 2 and 3 are fragmentary detailed cross-sectional views greatly enlarged of two embodiments of needle ends.

It is also possible, according to a modified embodiment of the invention, as shown in FIG. 3 of the accompanying drawing, to constitute the heating means 3 in the form of a thin composite layer 13' of a resistive material covering integrally the body of the needle except for the upper end of its head, this composite layer being itself covered by an electrically conductive layer 14. Such a material can preferably be either a resin of the loaded polytetrafluoroethylene type, loaded for example with black carbon powder or a metallic powder, or a conductive epoxyde resin of the type known by the commercial name EPO-TEK H20E or EPO-TEK 417 of the EPOTECNY company.

In such an embodiment, the external conductive layer 14 remains totally separated from the body of the needle 1 by the resin constituting the layer 13', and this layer 14 also covers the end of the point of the needle 1. Moreover, the external conductive layer 14 can then have an almost zero resistance, because it is not used. As a result, an electric current, passing between the body of the needle 1 and the external layer 14, will pass through the resistive layer 13' over all the extent of its mass.

According to another modified embodiment of the invention, the heating means 3 is present in the form of a thin resistive envelope, whose resistance diminishes progressively from the head of the needle 1 to its point. As a result, it is possible to provide a progressive falloff of thermal energy, which corresponds to a progressive decrease of the temperature, from the head toward the point of the needle, contrary to the embodiment described above, in which the loss is uniform. Thus, the needle will behave in a manner identical to a conventional acupuncture needle heated by any traditional external means.

The resistance of the resistive envelope can for example be comprised between 10 ohms in the case of a construction in the form of an external metallic layer, and 100 ohms in the case of an embodiment of the means 3 in the form of a thin composite layer 13' of a resistive material, this composite layer being itself covered with an electrically conductive layer 14.

A needle covered with such a complex has a mechanically stable surface and a thermally stable sub-layer and permits radiation into the air of variable energy, by modulation of the intensity within a bracket comprised between 20 mA and 200 mA for a resistance comprised between 10 ohms and 100 ohms, for one hour, without change of said covering.

The external energy source 2 is preferably present in the form of a receptacle provided at its lower portion with a recess 4 for reception and for electrical connection of head 1' at the end of the needle 1 and receiving in a chamber 5 a device 6, removable or fixed, for production of electric current, said chamber 5 being closed in a sealed manner by a cover 7, an electrically conductive wall 8 being provided between the recess 4 for the reception of the head 1', from which it is electrically insulated, and the chamber 5.

This receptacle can be provided at its end that receives the head 1' of the end of needle 1, with a means 9 for holding the head 1 of said needle 1 in its recess 4. This holding means 9 can be present in the form a disk sectors 10 mounted slidably at the base of the receptacle forming the energy source 2, against the action of return springs.

Preferably, the recess 5 has a depth such that, in case of closing the sectors of the disk 10 about the head 1' of the needle 1, the upper end of said head 1' of the needle 1 is applied against the electrically conductive wall 8 provided between the chamber 5 for reception of the device 6 for electrical production, and the recess 4.

The conductive wall 8 is mounted on the bottom of the receptacle forming the energy source 2 by means of an insulating cylinder 11 and is insulated from the recess 4 by an insulating plate 12. Thus, the electricity produced by the device 6 is transmitted, on the one hand, to the walls 8 and, on the other hand, to the recess 4 which is in contact with the conductive envelope of the heating means 3.

There results from the closure of the electrical circuit a heating of the resistive covering, over all its length, and a transfer of heat from the needle to the surrounding tissues.

The device 6 is constituted for example by an electric battery of the wafer battery type or else by an electrical accumulator. In such a case, it suffices, after emplacing the needle 1, to secure the energy source 2 on the head 1' of the needle 1, such that the means 3 of needle 1 is in electrical contact with the battery forming the device 6 by means of the conductive wall 8 and of the recess 4 and can heat itself.

There results a temperature increase of the assembly of the needle, such that the tissue in which the needle is implanted is subjected, over all the depth of penetration of the needle 1, to a corresponding constant heating over all the length or modulated over the latter. This has the effect of stimulating the deep layers of the organism and of the neurovascular complexes according to a temperature balancing principle similar to the operation of a cooling circuit. In particular, in the field of action of the needle, the micro-circulation of the blood is increased.

The needle according to the invention can be subjected, for treatment, to a temperature increase permitting dissipation in the tissues of sufficient energy, equivalent to that dissipated by a conventionally heated needle. This temperature increase can be obtained, in a known manner, by a choice of the optimum resistance of the heating means 3 and of the voltage delivered by the battery or the electrical accumulator. As a result, the modulation of the degree of heat to be obtained can be completely delimited.

Thanks to the invention, it is possible to provide heating, subcutaneously, at the point of acupuncture or of reflexotherapy, by means of an acupuncture needle having a flexibility comparable to that of conventional acupuncture needles and over all the length of the needle.

Moreover, the quantity of thermal energy dissipated is constant over the punctured neurovascular complex. One can thus carry out a non-exclusive single point stimulation, of variable depth and extent, by means of a portable and self-contained assembly not requiring an external connection by means of wires or other connections.

The duration of treatment with heat can be completely controlled by interruption of the production of heat directly by action on the external energy source or by separation of this source from the head 1' of the needle 1.

The needle 1 can have a straight shape or a curved shape as a function of the points of implantation and can have an end in the form of "seven stars" or "plum flower", which is to say ending in several points.

Moreover, the invention permits better carrying out of the technique of moxibustion, on the one hand, in terms of comfort for the patient and, on the other hand, in technical terms for the practitioner. Thus, the invention permits treatment permitting ambulatory treatment, as well as accessibility to several cutaneous regions simultaneously. Moreover, the practitioner is no longer required to be constantly present, because the risk from burning is eliminated and the sources of energy used have sufficient autonomy for overall duration of treatment.

The puncture depth can also be selected completely freely because of the fact that the external energy source 2 gives rise to no risk of burning and an inclination of the needle, if desired, with said external energy source 2 toward the skin remains harmless. The treatment of the hairy regions can also be carried out without preliminary preparation by shaving. This advantage permits particularly the use of acupuncture with moxa in veterinary treatments.

Finally, the needle according to the invention, with its source of energy, is completely clean in use, namely it gives off no pollution and can be coupled, contrary to the traditional technique, with the use of suction.

The heating acupuncture needle according to the invention has uses in other fields and, in a particularly interesting manner, in obstetrics and rheumatology. Thus, in the field of obstetrics, the invention could permit the use of a heating myorelaxant before enduring labor. In rheumatology, the invention is applicable for pathologies connected to cold, such as torticollis and lumbago, and even arthritis. The same is true as to gastro-enterology and pneumology.

Of course, the invention is not limited to the embodiment described and shown in the accompanying drawings. Modifications remain possible, particularly as to the construction of the various elements or by the substitution of technical equivalents, without thereby departing from the scope of protection of the invention.

What is claimed is:

1. A heating acupuncture needle, comprising: a needle having a tip; a source of external energy which heats a heating means, the heating means extending over at least most of the length of the needle and comprising an electrically conductive envelope surrounding the needle and covering the tip, but leaving an upper end of the needle uncovered.

2. The needle according to claim 1, further comprising an electrically insulating layer between said electrically conductive envelope and the needle.

3. The needle according to claim 2, wherein said electrically insulating layer surrounds the tip of the needle.

4. The needle according to claim 2, wherein said electrically insulating layer exposes the tip of the needle.

5. The needle according to claim 2, wherein the thickness of the electrically insulating layer and electrically conductive envelope together comprise less than 10% of the diameter of the needle.

6. The needle according to claim 2, wherein the electrically insulating layer is a resin.

7. A heating acupuncture needle, comprising: a needle having a tip; a source of external energy which heats a heating means, the heating means extending over at least most of the length of the needle and comprising an electrically conductive envelope surrounding the needle but leaving an upper end of the needle uncovered; an electrically insulating layer between said electrically conductive envelope and said needle; said electrically insulating layer surrounding the tip of the needle.

8. The needle according to claim 7, wherein the thickness of the electrically insulating layer and electrically conductive envelope together comprise less than 10% of the diameter of the needle.

9. The needle according to claim 7, wherein the electrically insulating layer is a resin.

* * * * *